US011370838B2

(12) United States Patent
Franklin et al.

(10) Patent No.: US 11,370,838 B2
(45) Date of Patent: Jun. 28, 2022

(54) METHODS OF CONJUGATING AN AGENT TO A THIOL MOIETY IN A PROTEIN THAT CONTAINS AT LEAST ONE SULFIDE BOND

(71) Applicant: GENENTECH, INC., South San Francisco, CA (US)

(72) Inventors: Jayme Franklin, South San Francisco, CA (US); Xin Xin Lin, South San Francisco, CA (US); Jeffrey Gorrell, South San Francisco, CA (US); Timothy Tully, South San Francisco, CA (US); Matthew Hutchinson, South San Francisco, CA (US); Charity Tucker Bechtel, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 529 days.

(21) Appl. No.: 15/414,330

(22) Filed: Jan. 24, 2017

(65) Prior Publication Data
US 2017/0209593 A1    Jul. 27, 2017

Related U.S. Application Data

(63) Continuation of application No. PCT/US2015/040931, filed on Jul. 17, 2015.

(60) Provisional application No. 62/028,679, filed on Jul. 24, 2014.

(51) Int. Cl.
*A61K 38/07* (2006.01)
*C07K 16/28* (2006.01)
*C07K 1/113* (2006.01)
*A61K 47/65* (2017.01)
*A61K 47/68* (2017.01)

(52) U.S. Cl.
CPC .......... *C07K 16/2803* (2013.01); *A61K 38/07* (2013.01); *A61K 47/65* (2017.08); *A61K 47/6803* (2017.08); *A61K 47/6811* (2017.08); *A61K 47/6849* (2017.08); *A61K 47/6889* (2017.08); *C07K 1/1133* (2013.01)

(58) Field of Classification Search
CPC .. C07K 16/2803; C07K 1/1133; A61K 38/07; A61K 47/6803
USPC ...................................................... 424/178.1
See application file for complete search history.

(56) References Cited

U.S. PATENT DOCUMENTS

| | | |
|---|---|---|
| 4,179,337 A | 12/1979 | Davis et al. |
| 4,495,285 A | 1/1985 | Shimizu et al. |
| 4,609,546 A | 9/1986 | Hiratani |
| 4,766,106 A | 8/1988 | Katre et al. |
| 5,116,949 A | 5/1992 | Nakajima |
| 5,622,929 A | 4/1997 | Willner |
| 5,641,870 A | 6/1997 | Rinderknecht et al. |
| 6,214,345 B1 | 4/2001 | Firestone et al. |
| 7,232,894 B1 | 6/2007 | Hemmendorff et al. |
| 7,659,241 B2 | 2/2010 | Senter et al. |
| 7,829,531 B2 | 11/2010 | Senter et al. |
| 7,851,437 B2 | 12/2010 | Senter et al. |
| 8,088,378 B2 | 1/2012 | Chen |
| 8,545,850 B2 | 10/2013 | Chen |
| 8,722,857 B2 | 5/2014 | Chen |
| 9,845,355 B2 | 12/2017 | Chen |
| 9,896,506 B2 | 2/2018 | Chen |
| 2005/0276812 A1 | 12/2005 | Ebens et al. |
| 2009/0028856 A1 | 1/2009 | Chen |
| 2009/0068202 A1 | 3/2009 | Chen |
| 2009/0194731 A1 | 8/2009 | Hurd et al. |
| 2010/0160236 A1 | 6/2010 | Becker et al. |
| 2010/0215669 A1 | 8/2010 | Chen |
| 2011/0097322 A1 | 4/2011 | Alley et al. |
| 2011/0135667 A1 | 6/2011 | Chen |
| 2012/0282279 A1 | 11/2012 | Das et al. |
| 2012/0322686 A1 | 12/2012 | Lyon et al. |
| 2013/0295007 A1 | 11/2013 | Chen |
| 2014/0099260 A1 | 4/2014 | Chen |
| 2014/0127197 A1 | 5/2014 | Ebens et al. |
| 2014/0128580 A1 | 5/2014 | Ebens et al. |
| 2014/0335107 A1 | 11/2014 | Chen |
| 2015/0314016 A1 | 11/2015 | Chen |
| 2017/0058032 A1 | 3/2017 | Chen |
| 2018/0201679 A1 | 7/2018 | Chen |

FOREIGN PATENT DOCUMENTS

| | | |
|---|---|---|
| CN | 1723219 A | 1/2006 |
| EP | 2641618 | 9/2013 |
| JP | 1990076899 A | 3/1990 |
| JP | H02076899 A | 3/1990 |
| JP | 1990218700 A | 8/1990 |
| JP | H02218700 A | 8/1990 |
| JP | H0625012 A | 2/1994 |
| JP | 1999124395 A | 5/1999 |

(Continued)

OTHER PUBLICATIONS

Extended European Search Report for European Patent Application No. 15824358.4, dated Mar. 6, 2018, 11 pages.
Official Action (with English translation only) for Russian Patent Application No. 2017105428, dated May 11, 2018, 6 pages.
Official Action for Singapore Patent Application No. 11201700365T, dated Mar. 21, 2018, 10 pages.
Official Action for Canada Patent Application No. 2,955,007, dated Feb. 16, 2018 5 pages.

(Continued)

*Primary Examiner* — Yan Xiao
(74) *Attorney, Agent, or Firm* — Morrison & Foerster LLP

(57) ABSTRACT

The invention provides improved methods of conjugating an agent to a thiol moiety in a protein that contains at least one disulfide bond and at least one trisulfide bond. Exemplary embodiments include the production of antibody drug conjugates substantially free of impurities created in the presence of reactive sulfide moieties in the production processes.

19 Claims, 7 Drawing Sheets

(56) References Cited

FOREIGN PATENT DOCUMENTS

| | | | |
|---|---|---|---|
| JP | 2003500053 A | 1/2003 | |
| JP | 2004530651 A | 10/2004 | |
| JP | 2006518753 A | 8/2006 | |
| JP | 2008525517 A | 7/2008 | |
| JP | 2010509192 A | 3/2010 | |
| JP | 2014042522 A | 3/2014 | |
| RU | 2511410 | 4/2014 | |
| WO | WO 96/02570 | 2/1996 | |
| WO | WO 00/02900 | 1/2000 | |
| WO | 200071716 A2 | 11/2000 | |
| WO | 200071716 A3 | 7/2001 | |
| WO | 2002062827 A2 | 8/2002 | |
| WO | WO 2004/010957 | 2/2004 | |
| WO | WO 2004/031213 | 4/2004 | |
| WO | 2002062827 A3 | 5/2004 | |
| WO | WO2004073656 A2 | 9/2004 | |
| WO | WO2004073656 A3 | 2/2005 | |
| WO | WO2005047336 A1 | 5/2005 | |
| WO | WO2006069940 A1 | 7/2006 | |
| WO | 2008027944 A2 | 3/2008 | |
| WO | 2008027944 A3 | 7/2008 | |
| WO | WO 2008/141044 | 11/2008 | |
| WO | WO2009012256 A1 | 1/2009 | |
| WO | WO2009012268 A1 | 1/2009 | |
| WO | WO2009099728 A1 | 8/2009 | |
| WO | WO 2011/041721 | 4/2011 | |
| WO | WO 2012/158551 | 11/2012 | |
| WO | WO 2013/060867 | 5/2013 | |
| WO | WO2013093809 A1 | 6/2013 | |
| WO | WO 2013/190292 | 12/2013 | |

OTHER PUBLICATIONS

Andersson et al., "Isolation and characterization of a trisulfide variant of recombinant human growth hormone formed during expression in *Escherichia coli*," Int. J. Peptide Protein Res., 1996, vol. 47, pp. 311-321.

Breton et al., "Detection of traces of a trisulphide derivative in the preparation of a recombinant truncated interleukin-6 mutein," J. Chromatography A, 1995, vol. 709, pp. 135-146.

Canova-Davis et al., "Confirmation by Mass Spectrometry of a Trisulfide Variant in Methionyl Human Growth Hormone Biosynthesized in *Escherichia coli*," Anal. Chem., 1996, vol. 68, pp. 4044-4051.

Chandrasekhar et al., "Thiol-Disulfide Exchange in Peptides Derived From Human Growth Hormone," J. Pharm. Sci., 2004, vol. 103(4), 26 pages.

Cumnock et al., "Trisulfide Modification Impacts the Reduction Step in antibody-Drug Conjugation Process," Bioconjugate Chem., 2013, vol. 24, pp. 1154-1160 (7 pages).

Dubowchik et al., "Receptor-mediated and enzyme-dependent targeting of cytotoxic anticancer drugs," Pharmacology & Therapeutics, 1999, vol. 83, pp. 67-123.

Gu et al., "Characterization of Trisulfide Modification in Antibodies," Analytical Biochem, 2010, vol. 400, pp. 89-98.

Jespersen et al., "Characterisation of a trisulphide derivative of biosynthetic human growth hormone produced in *Escherichia coli*," Eur. J. Biochem., 1994, vol. 219, pp. 365-373.

Okado-Matsumoto et al., "Modification of Cysteine 111 in human Cu,Zn-superoxide dismutase," Free Radical Biol. & Med., 2006, vol. 41, pp. 1837-1846.

Pristatsky et al., "Evidence for Trisulfide Bonds in a Recombinant Variant of a Human IgG2 Monoclonal Antibody," Anal. Chem., 2009, vol. 81, pp. 6148-6155.

Wu et al., "Arming antibodies: prospects and challenges for immunoconjugates," Nature Biotechnology, 2005, vol. 23(9), pp. 1137-1146.

International Search Report and Written Opinion for International Patent Application No. PCT/US15/40931, dated Oct. 23, 2015, 22 pages.

International Preliminary Report on Patentability for International Patent Application No. PCT/US15/40931, dated Feb. 2, 2017, 21 pages.

Official Action for Canada Patent Application No. 2,955,007, dated Dec. 19, 2018, 5 pages.

U.S. Appl. No. 15/908,703, Chen et l., filed Feb. 28, 2018,(Copy not submitted herewith pursuant to the waiver of 37 C.F.R. § 1.98(a)(2)(iii) issued by the Office on Sep. 21, 2004).

METHODS OF CONJUGATING AN AGENT TO A THIOL MOIETY IN A PROTEIN THAT CONTAINS AT LEAST ONE SULFIDE BOND

CROSS REFERENCE TO RELATED APPLICATION DATA

This application is a continuation of PCT Application No. PCT/US2015/040931, having an international filing date of Jul. 17, 2015, which designated the United States, which PCT application claimed the benefit of U.S. Provisional Patent Application Ser. No. 62/028,679, filed Jul. 24, 2014, both of which are incorporated herein by reference in their entirety. Each of the applications and patents cited in this disclosure, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

BACKGROUND

Recombinant proteins have become an important class of therapeutic compounds employed for the treatment of a broad range of diseases. Recent successes in the field of biotechnology have improved the capacity to produce large amounts of such proteins. However, extensive characterization of the products demonstrates that the proteins are subject to considerable heterogeneity. For example, molecular heterogeneity can result from chemically-induced modifications such as oxidation, deamidation, and glycation as well post-translational modifications such as proteolytic maturation, protein folding, glycosylation, phosphorylation, and disulfide bond formation. Molecular heterogeneity is undesirable because therapeutic products must be extensively characterized by an array of sophisticated analytical techniques and meet acceptable standards that ensure product quality and consistency.

Antibodies (or immunoglobulins) are particularly subject to such structural heterogeneity due to the fact that they are large, multi-chain molecules. For example, IgG antibodies are composed of four polypeptide chains: two light chain polypeptides (L) and two heavy chain polypeptides (H). The four chains are typically joined by disulfide bonds that form between cysteine residues present in the heavy and light chains. These disulfide linkages govern the overall structure of the native $H_2L_2$ tetramer. Overall, IgG1 antibodies contain four interchain disulfide bonds, including two hinge region disulfides that link the H chains, and one disulfide bond between each heavy H and L chain.

Antibody-drug conjugates (ADCs) are monoclonal antibodies (mAbs) coupled to potent drug molecules, which combine the biological specificity of antibodies with the high potency of specific therapeutic compounds. The drug compounds can be coupled to antibodies using lysine- or cysteine-directed linker chemistry (Wu, A. M., Nat. Biotechnol. 23:1137-46 (2005)). Using cysteine-directed chemistry, drugs can either be linked to native cysteines derived from reduction of interchain disulfide bonds or to specially engineered cysteines. Stoichiometrically, one reduced disulfide bond should expose two free thiols for drug conjugation. When conjugation is to interchain cysteines of IgG1 molecules, the resulting conjugates are composed of mixtures containing predominantly species with 0, 2, 4, 6, or 8 drugs per antibody molecule. The average number of drug molecules conjugated per antibody (the drug to-antibody ratio; "DAR"), is an important quality attribute in ADC products, as the average DAR reflects the amount of drug delivered per dose, and therefore, may affect both the safety and efficacy of the ADC. Incomplete disulfide bond formation, or bond breakage via oxidation or beta-elimination followed by disulfide scrambling, are all potential sources of antibody heterogeneity. Additionally, trisulfide bond formation was been reported within the interchain, hinge region bonds of a human IgG2 antibody. (Pristatsky et al, Anal. Chem. 81:6148 (2009); Gu et al, Anal. Biochem. 400:89-98 (2010)). The trisulfide bond occurs when an extra sulfur atom forms a "trisulfide bridge" (—CH2-S—S—S—CH2-) within the molecule and may cause additional consistency and contamination problems during ADC production.

Trisulfide linkages have previously been detected in superoxide dismutase (Okado-Matsumoto et al., Free Radical Bio. Med. 41:1837 (2006)), a truncated form of interleukin-6 (Breton et al., J. Chromatog. 709:135 (1995)), and bacterially expressed human growth hormone (hGH) (Canova-Davis et al., Anal. Chem. 68:4044 (1996)). Other polypeptides containing disulfide bonds, e.g. insulin, interleukins and certain clotting factors (such as Factor VII) may also potentially form trisulfide derivatives.

In the case of hGH, it was speculated that trisulfide formation was promoted by $H_2S$ released during the fermentation process (PCT Patent Application No. WO 96/02570), and the trisulfide content of hGH was increased by exposure to $H_2S$ in solution (U.S. Pat. No. 7,232,894). The trisulfide derivatives of hGH have also been described in recombinant hGH formed during expression in *Escherichia coli* (Andersson et al., Int. J. Peptide Protein Res. 47: 311-321 (1996); A. Jesperson et al., Eur. J. Biochem. 219: 365-373 (1994)).

PCT Publication No. WO 96/02570 describes another method for converting the hGH trisulfide derivative back to the native form of hGH by treating the derivative with a sulfite compound, such as sodium sulfite, potassium sulfite or ammonium sulfite, or an alkaline-earth metal sulfite such as magnesium sulfite or calcium sulfite.

PCT Publication No. WO 00/02900 describes methods for the production of recombinant peptides with a low amount of trisulfides, characterized by the addition of a metal salt (e.g. potassium or sodium salt) during or after the fermentation step.

PCT Publication No. WO 04/31213 discloses methods for decreasing the amount of a trisulfide isoform impurity produced in recombinant production of a "growth hormone antagonist polypeptide" in genetically modified host cells, wherein the impurity is contacted with a "mercapto compound" (such as sulfites, glutathione, β-mercapto-ethanol, dithiothreitol, cysteine). The application also discloses the use of chelating agents or metal salts to achieve a reduction in the amount of trisulfide formed.

Unfortunately, removal of trisulfide bonds by exposure to cysteine, mercapto compounds, sulfite compounds, metal salts, and the like, in solution or during the fermentation processes, has several drawbacks, in particular for large scale processing. For example, large quantities of these compounds are required. Additionally, as many of these chemicals have known toxicities, such methods also necessitate further processing step(s) to remove the chemicals from the proteins after trisulfide bonds are removed, and introduce another source of potential impurities and process variability. In addition, removal of trisulfide bonds by exposure to such chemicals in solution can promote aggregation through the formation of undesirable disulfide linkages.

Therefore, in order to address variability and contamination caused by the presence of trisulfide bonds during production and purification procedures used in the manufacture of in recombinant proteins (including the production of antibodies and ADCs), efficient and improved means for reducing or eliminating such variability and/or impurities are provided by the methods disclosed herein.

SUMMARY OF THE EMBODIMENTS

Antibody-drug conjugates (ADCs) with interchain cysteine linkages are generated by reducing a fraction of the total interchain disulfide bonds. The newly available free thiols are then conjugated with the drug molecule (which is often already part of a larger linker-drug intermediate). As partial reductions are performed under nondenaturing conditions, linkage to cysteines participating in intrachain disulfide bonds is typically not observed. The linker-drug containing the thiol reactive moiety (such as a maleimide) is added in excess to ensure conjugation of all available free thiols. Tris(2-carboxyethyl)phosphine (TCEP) is a preferred reductant in these processes due to its favorable reaction kinetics, solution stability prior to reaction, and because it cannot form mixed disulfides with antibody thiols. One molecule of TCEP is expected to reduce one disulfide bond, exposing two free thiols for drug conjugation. Following reduction with one molar equivalent of TCEP (1.0×TCEP:mAb), the expected average DAR value is 2.0. Similarly, in order to achieve a targeted average DAR value of 4.0, a predicted TCEP addition of 2 mol equiv (2.0×TCEP:mAb) would be required. In practice, the reduction step is performed using a predetermined TCEP:antibody (TCEP:mAb) molar ratio.

During the development of multiple cysteine-directed ADC products, deviations from the theoretical predictions of average DAR values were observed and have been reported (Cumnock, et al. Bioconjugate Chem. 24:1154-60 (2013)). In these instances, the required ratio of reductant to antibody, although reproducible for a given lot of antibody, varied between antibodies as well as between different lots of the same antibody. Although some antibody lots required amounts of TCEP very close to the theoretical predictions, most lots required an increased TCEP:mAb molar ratio to achieve the targeted average DAR value. The presence of trisulfide bonds was identified as a potential source of this variability observed during the manufacture of ADCs. Trisulfides were identified as a potential source of the TCEP:mAb ratio variability observed during the manufacture of these ADCs.

Additionally, reverse-phase HPLC analysis identified unexpected impurities in several compositions containing the conjugated ADCs. Investigation of the ADCs and impurities indicated that reactive sulfide moieties present in the conjugation reaction between the antibody and the drug molecules as a result of the reduction of trisulfide bonds present in the antibodies, were participating in the formation of free drug dimers, which turned out to be the impurities in these compositions.

Rather than modify the established and certified recombinant techniques used to produce the antibodies, the inventors have developed methods of reducing free drug dimer (and other impurities) formation that occurs in the reduction of recombinant proteins containing trisulfide bonds by reducing or eliminating reactive sulfide species from these compositions during reduction and/or conjugation reactions.

Thus, in one aspect, the invention provides methods of conjugating an agent to a thiol moiety in a protein that contains at least one disulfide bond and at least one trisulfide bond, including reducing at least one sulfide bond in an isolated protein to form a composition comprising a reactive sulfide and a reduced protein containing at least one thiol group, and decreasing the reactive sulfide content of the resulting composition. An agent is then conjugated to the at least one thiol group of the reduced protein to form a protein-agent conjugate.

The step of reducing at least one sulfide bond may include at least partial reduction of the at least one sulfide bond by contacting the isolated protein with a reducing agent.

The isolated protein may include at least four disulfide bonds.

The isolated protein may also include at least two trisulfide bonds.

Prior to the reducing step, between about 1% and about 20% of the sulfide bonds in the isolated protein may be trisulfide bonds. Prior to the reducing step, between about 5% and about 7% of the sulfide bonds in the isolated protein may be trisulfide bonds.

The reducing step may be conducted under non-denaturing conditions. In these reactions, the reducing agent may be at least one of dithiothreitol (DTT), beta-mercaptoethanol (βME), tris(2-carboxyethyl)phosphine (TCEP), cysteine, L-cysteine, reduced glutathione (GSH) and L-GSH. The reducing agent may be TCEP, and the TCEP may be mixed with the isolated protein in a predetermined molar ratio of TCEP to the isolated protein. The predetermined molar ratio of TCEP to the isolated protein may be a molar excess of TCEP.

The step of reducing at least one sulfide bond in the protein includes contacting the isolated protein with a chemical reducing agent in a concentration of about 0.1 to about 8 mM; about 0.1 to about 5 mM; about 0.1 to about 3 mM; about 0.1 to about 1 mM; about 8 mM; about 5 mM; about 3 mM; about 1 mM; and, about 0.5 mM.

The step of reducing at least one sulfide bond in the protein may be conducted at a pH between about 5.0 and about 8.0; between about 5.5 and about 7.5; about 5.5 or about 6.5.

Prior to the reducing step, the pH of the isolated protein may be adjusted to a pH between about 5.0 and about 8.0.

Preferably, about 100% of the trisulfide bonds in the protein are reduced.

Subsequent to the reducing step, between about 4 and about 8 moles of thiol moieties may be available for conjugating with the agent, for every mole of isolated protein reduced.

The step of decreasing the reactive sulfides in the composition may include adjusting the pH of the composition to a pH between about 5.0 and about 6.0, which may include reducing the pH of the composition to a pH of about 5.5.

The step of decreasing the reactive sulfides in the composition may include removing liquid media from the composition and replacing the liquid media with a replacement liquid media. The liquid media may include a buffer.

The step of decreasing the reactive sulfides in the composition may include allowing the reduced protein in the composition to associate with a solid support before replacing at least 90% of the composition with a replacement solution lacking the reactive sulfide. The solid support may include at least one of a filter membrane, a selectively permeable membrane, and a chromatography resin.

The step of decreasing the reactive sulfides in the composition may include mixing the composition in the reducing step at a rate sufficient to reduce the reactive sulfide content of the composition. The mixing may include stirring the composition at an increased rate in excess of an optimal rate of mixing in order to reduce sulfide bond(s) in the isolated protein. The mixing at an increased rate may include increasing the mixing rate in the reducing step for a period of time that is less than the full reaction time for the reducing step.

The step of decreasing the reactive sulfides in the composition may include contacting the solution with a nitrogen source. The nitrogen source may include nitrogen gas, which may be bubbled through the composition. The contacting may also include sparging the composition with at least one of nitrogen gas, air, and argon gas. The contacting may be conducted for a period of time between about 1 minute and about 240 minutes. The contacting may also include sparging the composition with nitrogen gas at a rate between about 10 cubic centimeters per minute and about 60 cubic centimeters per minute. The contacting may also include mixing the composition in the presence of nitrogen gas at a rate that is at least 200% greater than the optimal mixing rate for the reducing step.

The contacting step may be conducted at a pH between about 5.0 and about 8.0. The contacting may be conducted at a temperature between about 4° C. and about 40° C. The contacting may also be conducted at a temperature between about 15° C. and about 40° C. The contacting may also be conducted at a temperature of about 20° C. The contacting may also be conducted at a temperature of about 30° C. The ratio of the surface area to the volume of the composition may be about 2. The contacting may include piping nitrogen gas against a side of a reaction vessel containing the composition. The contacting may include submersing a sparge stone in the composition, wherein the sparge stone has a diameter between about 1 cm and about 1 meter.

The contacting may include introducing a nitrogen gas into the composition during the reducing step for a time that is less than the time for conducting the reducing step. The contacting step may be conducted in a closed reaction vessel. The contacting may be conducted in an open reaction vessel, such that reactive sulfide(s) is vented from the composition.

The contacting is conducted in the presence of at least one of a tween and an antifoaming agent. The tween may be at least one of Tween20 and Tween-80. The antifoaming agent may be at least one of Antifoam-A, Antifoam-C, and a poloxamer such as polyethylene oxide.

The isolated protein may be an antibody or antibody fragment. The antibody fragment may be an antigen-binding antibody fragment, including for example, a Fab, a Fab', a F(ab)$_2$, a Fv fragment, a diabody, a single-chain antibody, an scFv fragment or an scFv-Fc.

The antibody or antibody fragment may be an IgG antibody. The antibody or antibody fragment may also be a human monoclonal antibody.

The antibody or antibody fragment may include a human immunoglobulin constant region. The constant region may be a human IgG constant region. In specific embodiments, the isotype of the IgG constant region is IgG1, IgG2, IgG3, or IgG4.

The sulfide bonds in an antibody or antibody fragment are between antibody heavy and light chains, or between antibody heavy chains, or between both antibody heavy and light chains and between antibody heavy chains. The antibody or antibody fragment may include a light chain constant domain. The light chain constant domain may be a kappa constant domain. The antibody may also be an IgG1 monoclonal antibody which has 4 interchain sulfide bonds comprising two sulfide bonds in the hinge region connecting heavy chains, and one sulfide bond between each light chain and heavy chain.

The isolated protein may be an antibody, and the reducing step may result in reducing only interchain disulfide bonds and no intrachain bonds.

The agent may be at least one therapeutic agent selected from a chemotherapeutic agent, a nucleic acid, a cytokine, an immunosuppressant, a radioisotope, an antibiotic, and a therapeutic antibody. The agent may also be at least one anti-tubulin agent selected from an auristatin, a vinca alkaloid, a podophyllotoxin, a taxane, a baccatin derivative, a cryptophysin, a maytansinoid, a combretastatin, and a dolastatin. The dolastatin may be an auristatin. The auristatin may also be monomethyl auristatin E (MMAE) or monomethyl auristatin F (MMAF).

The agent may be at least one of a DNA minor groove binding agent, a DNA minor groove alkylating agent, an enediyne, a lexitropsin, a duocarmycin, a taxane, a puromycin, a dolastatin, a maytansinoid, and a vinca alkaloid.

The agent may be a linker moiety adapted to link the at least one thiol group of the reduced protein to the agent. The linker moiety may be a cleavable linker or a non-cleavable linker. The linker moiety may be a linker susceptible to cleavage under intracellular conditions. The linker moiety may be a peptide linker cleavable by an intracellular protease. The linker moiety may be a dipeptide linker. The dipeptide linker may be a valine-citrulline (val-cit) or a phenylalanine-lysine (phe-lys) linker. The dipeptide linker may be a maleimide functional group that reacts with free thiols to form a covalent bond.

The protein-agent conjugate may be one of aCD22-val-cit-MMAE, aCD22-val-cit-MMAF, aLy6E-val-cit-MMAE, aLy6E-val-cit-MMAF, aCD79b-val-cit-MMAE, aCD79b-val-cit-MMAF, aNaPi2b-val-cit-MMAE, aNaPi2b-val-cit-MMAF, aMUC16-val-cit-MMAE, a MUC16-val-cit-MMAF, aSTEAP1, and aETBR.

Another aspect of the invention provides a method for converting trisulfide bonds to disulfide bonds in an isolated antibody, including contacting at least one isolated antibody containing at least one trisulfide bond in a solution with TCEP at a pH between about 5.5 and about 7.5, and contacting the solution with nitrogen gas. The isolated antibody is then conjugated to an auristatin, or a derivative thereof, to form an antibody-drug conjugate (ADC).

Additional embodiments of the disclosed methods, and compositions are set forth, at least in part, in the description that follows, can be understood from the description, or may be learned by practicing the disclosed methods and compositions. The foregoing brief description and the following detailed description are exemplary and explanatory and are not restrictive of the invention as claimed.

BRIEF DESCRIPTION OF THE DRAWINGS

FIG. 1A shows the free drug analysis of the in-process conjugation pool for aCD79b-vcMMAE, containing no trisulfides in the starting mAb intermediate (control), and FIG. 1B shows the same analysis for aCD22-vcMMAE, containing about 5-6% of measured trisulfides in the starting mAb intermediate.

FIG. 1A shows free drug analysis of the in-process conjugation pool for aCD79b-vcMMAE, containing no trisulfides in the starting mAb intermediate (control), and FIG. 1B shows the same analysis for aCD22-vcMMAE, containing about 5-6% of measured trisulfides in the starting mAb intermediate.

FIG. 4A shows free drug in the in-process conjugation pool for aCD22-vcMMAE, with (bottom line) and without (top line) N2 sparging during the last 5 minutes of the partial reduction reaction. FIG. 4B shows the free drug analysis of the conjugation pool for aLy6E-vcMMAE, with (bottom line) and without (top line) N2 sparging during the last 5 minutes of the TCEP partial reduction reaction.

FIG. 5A shows the results from reactions reduced with TCEP, and FIG. 5B shows the results for reactions reduced with DTT.

DETAILED DESCRIPTION

Figure 1A:
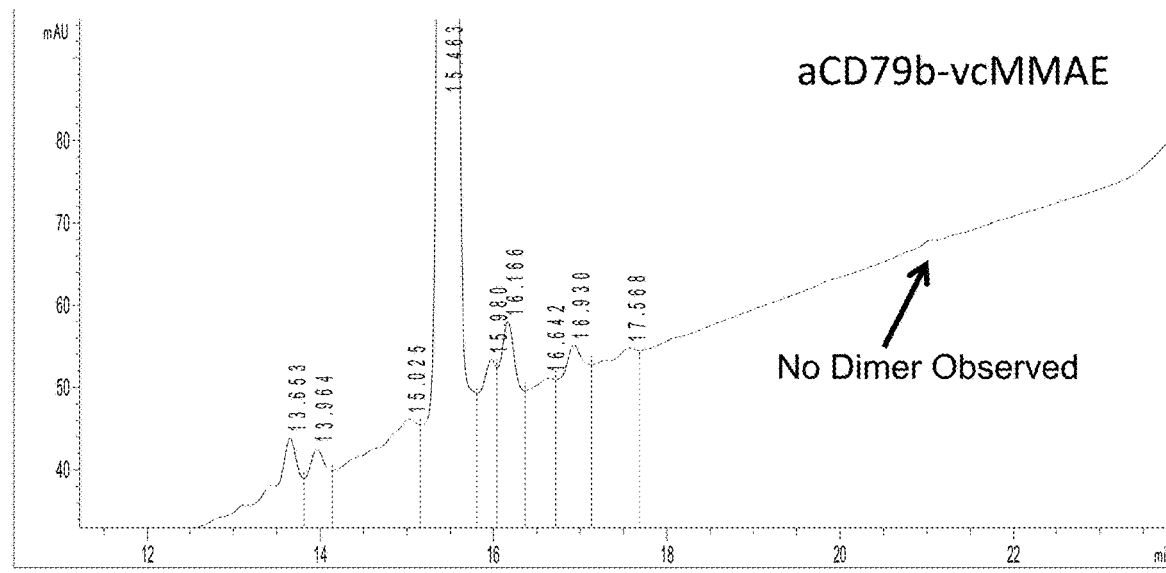
FIGS. 1A and 1B show the measurement of free-drug dimer by RP-HPLC after partial reduction reactions and subsequent conjugation reactions were performed using mAb intermediates containing different percentages of trisulfides.

Reference will now be made in detail to representative embodiments of the invention. While the invention will be described in conjunction with the enumerated embodiments, it will be understood that the invention is not intended to be limited to those embodiments. On the contrary, the invention is intended to cover all alternatives, modifications, and equivalents that may be included within the scope of the present invention as defined by the claims.

One skilled in the art will recognize many methods and materials similar or equivalent to those described herein, which could be used in and are within the scope of the practice of the present invention. The present invention is in no way limited to the methods and materials described.

Definitions

Unless defined otherwise, technical and scientific terms used herein have the same meaning as commonly understood by one of ordinary skill in the art to which this invention belongs. Although any methods, devices, and materials similar or equivalent to those described herein can be used in the practice or testing of the invention, the preferred methods, devices, and materials are now described.

As used in this application, including the appended claims, the singular forms "a," "an," and "the" include plural references, unless the content clearly dictates otherwise, and are used interchangeably with "at least one" and "one or more." Thus, reference to "a polynucleotide" includes a plurality of polynucleotides or genes, and the like.

As used herein, the term "about" represents an insignificant modification or variation of the numerical value, such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

Reference herein to any numerical range (for example, a dosage range) expressly includes each numerical value (including fractional numbers and whole numbers) encompassed by that range. For example, reference herein to a range of "less than x" (wherein x is a specific number) includes whole numbers x−1, x−2, x−3, x−4, x−5, x−6, etc., and fractional numbers x−0.1, x−0.2, x−0.3, x−0.4, x−0.5, x−0.6, etc. In yet another illustration, reference herein to a range of from "x to y" (wherein x is a specific number, and y is a specific number) includes each whole number of x, x+1, x+2 . . . to y−2, y−1, y, as well as each fractional number, such as x+0.1, x+0.2, x+0.3 . . . to y−0.2, y−0.1. In another example, the term "at least 95%" includes each numerical value (including fractional numbers and whole numbers) from 95% to 100%, including, for example, 95%, 96%, 97%, 98%, 99% and 100%.

By "therapeutic" agent is meant a compound or composition effective to produce a desired therapeutic response in an individual.

Proteins suitable for use in the methods of the present invention include proteins of natural or synthetic (i.e., recombinant) origin, and the methods according to the invention may be applied to proteins extracted from any source, e.g. from a plant or an animal. The proteins may be therapeutic proteins, as defined above, and usually contain one or more disulfide bonds, and one or more trisulfide bonds. Exemplary proteins include superoxide dismutase, interleukin, growth hormones and antibodies or antibody fragments.

Reactive sulfides may include hydrogen sulfide ($H_2S$) and/or deprotonated forms thereof (i.e. $HS^-$ and/or $S_2^-$).

"Trisulfide bonds" are generated by the insertion of an additional sulfur atom into a disulfide bond, thereby resulting in the covalent bonding of three consecutive sulfur atoms. Trisulfide bonds can form between cysteine residues in proteins and can form intramolecularly (i.e., between two cysteines in the same protein) or intermolecularly (i.e. between two cysteines in separate proteins). In the case of antibodies, such as IgG1 antibodies, two intermolecular disulfide bonds link the heavy chains together and an intermolecular disulfide bonds also links each of the heavy and light chains. Similarly, IgG2 molecules contain three intermolecular disulfide bonds that link the heavy chains, and IgG3 molecules contain 6-16 intermolecular disulfide bonds that link the heavy chains. Trisulfide modifications can occur at either of these disulfide linkages, but occur more frequently at the heavy-light (HL) link than at the heavy-heavy (HH) link.

It is believed that chemical reduction of trisulfide bonds in proteins releases reactive sulfide species, which may induce the formation of drug and protein dimers or other unwanted and potentially dangerous derivatives. While it is not often feasible to prevent the formation of a trisulfide bond or eliminate all existing trisulfide bonds in a protein, the present inventors have discovered that it is possible to reduce or eliminate the formation of drug and/or protein impurities (i.e. unwanted chemical reaction products) during protein reduction in conjugation reactions. The method of reducing or eliminating these unwanted chemical reaction products includes removal of reactive sulfide species from the liquid medium of the chemical reaction.

Reduction of Isolated Proteins

Proteins containing disulfide and trisulfide bonds, useful in the methods of the present invention may be obtained by a variety of methods which include, but are not limited to, isolation from a natural source (in the case of naturally occurring proteins), recombinant protein production methodologies that may include site-directed (or oligonucleotide-mediated) mutagenesis and cassette mutagenesis of an earlier prepared DNA encoding the polypeptide. Mutagenesis protocols, kits, and reagents are commercially available, e.g. QuikChange™ Multi Site-Direct Mutagenesis Kit (Stratagene, La Jolla, Calif.).

The isolated proteins may be chemically synthesized using known oligopeptide synthesis methodology or may be prepared and purified using recombinant technology. The appropriate amino acid sequence, or portions thereof, may be produced by direct peptide synthesis using solid-phase techniques (Stewart et al., Solid-Phase Peptide Synthesis, (1969) W. H. Freeman Co., San Francisco, Calif.; Merrifield, (1963) J. Am. Chem. Soc., 85:2149-2154). In vitro protein synthesis may be performed using manual techniques or by automation. Automated solid phase synthesis may be accomplished, for instance, employing t-BOC or Fmoc protected amino acids and using an Applied Biosystems Peptide Synthesizer (Foster City, Calif.) using manufacturer's instructions. Various portions of the isolated protein may be chemically synthesized separately and combined using chemical or enzymatic methods to produce the desired isolated protein for use in the methods of this invention.

Additionally, protein fragments, including antibody fragments, may be used as the isolated protein in the methods of this invention. Traditionally, antibody fragments were derived via proteolytic digestion of intact antibodies (Morimoto et al (1992) Journal of Biochemical and Biophysical Methods 24:107-117; and Brennan et al (1985) Science, 229:81), or produced directly by recombinant host cells. Fab, Fab', F(ab)$_2$, Fv fragments, diabody, single-chain antibody, scFv fragments or scFv-Fc antibody fragments can all be expressed in, and secreted from E. coli, thus allowing the facile production of large amounts of these fragments. Antibody fragments can be isolated from antibody phage libraries. Alternatively, Fab'-SH fragments can be directly recovered from E. coli and chemically coupled to form F(ab')$_2$ fragments (Carter et al (1992) Bio/Technology 10:163-167), or isolated directly from recombinant host cell culture. The antibody may be a single chain Fv fragment (scFv). The antibody fragment may also be a "linear antibody" (U.S. Pat. No. 5,641,870). Such linear antibody fragments may be monospecific or bispecific. The antibody or antibody fragment may be an IgG antibody. The antibody may be a human monoclonal antibody.

The isolated antibody may also be a cysteine engineered antibody, which enables antibody conjugate compounds, such as antibody-drug conjugate (ADC) compounds, with drug molecules at designated, designed, selective sites. Reactive cysteine residues on an antibody surface allow specifically conjugating a drug moiety through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are typically required (Garman, 1997, Non-Radioactive Labelling: A Practical Approach, Academic Press, London).

In the embodiments in which antibodies containing di- and trisulfide bonds are used, an antibody may have only one or several sulfide bonds which may be reduced to form sufficiently reactive thiol groups through which a drug may be conjugated. The protein may be an IgG1 monoclonal antibody which has a total of 4 interchain disulfides: two in the hinge region connecting the heavy chains, and one between each light chain and heavy chain near the Fab region. Each reduced interchain disulfide bond results in two free thiols, each available for conjugation with a drug. Reduction of such antibody intermediate in non-denaturing conditions will typically reduce only the interchain disulfide bonds and not the intrachain bonds. Thus, complete reduction of the interchain disulfide bonds results in a total of 8 moles of free thiols per mole of IgG1 antibody intermediate.

The antibody may have a human immunoglobulin constant region. The antibody or antibody fragment may include a human IgG constant region, and the isotype of the IgG constant region may be IgG1, IgG2, IgG3, or IgG4. In specific embodiments, the isotype of the IgG constant region is IgG1.

The sulfide bonds present in the antibody or antibody fragment are between antibody heavy and light chains, or between antibody heavy chains, or between both antibody heavy and light chains and between antibody heavy chains. The antibody or antibody fragment may include a light chain constant domain. The light chain constant domain may be a kappa constant domain. The antibody may be an IgG1 monoclonal antibody which has 4 interchain sulfide bonds comprising two sulfide bonds in the hinge region connecting heavy chains, and one sulfide bond between each light chain and heavy chain.

Typically, only a subset of the sulfide bonds in a protein are present as trisulfide bonds. Between about 1% and about 20% of the sulfide bonds in the isolated protein may be trisulfide bonds, alternatively, between about 1% and about 18%, between about 2% and about 16%, between about 3% and about 12%, between about 4% and about 10%, or between about 5% and about 7% of the sulfide bonds in the isolated protein are trisulfide bonds. At least about 80% of the trisulfide bonds in the isolated protein may be reduced in the reducing step, alternatively at least about 81%, 82%, 83%, 84%, 85%, 86%, 87%, 88%, 89%, 90%, 91%, 92%, 93%, 94%, 95%, 96%, 97%, 98%, 99% or 100% of the trisulfide bonds in the isolated protein are reduced in the reducing step.

The isolated proteins, including antibodies, are reduced under partial or total reducing conditions, to generate reactive cysteine thiol groups. The reducing agent may include at least one of dithiothreitol (DTT), beta-mercaptoethanol (βME), tris(2-carboxyethyl) phosphine (TCEP), cysteine, L-cysteine, reduced glutathione (GSH) and L-GSH. When antibodies are used in these methods, the reducing agent is preferably one or both of dithiothreitol (DTT) and tricarbonylethylphosphine (TCEP) and the reducing reaction is carried out under non-denaturing conditions. The TCEP is typically used in the reducing reaction at a predetermined molar ratio of TCEP to the isolated protein. Typically, the TCEP is added to the reaction in a molar excess to the isolated protein. The TCEP may be added to the reducing reaction in a concentration of about 0.1 to about 8 mM; about 0.1 to about 5 mM; about 0.1 to about 3 mM; about 0.1 to about 1 mM; about 8 mM; about 5 mM; about 3 mM; about 1 mM; or about 0.5 mM. In using isolated antibodies, subsequent to the reducing step, typically between about 4 and about 8 moles of thiol moieties are available for conjugating with the agent, for every mole of isolated protein reduced.

The reducing reaction may be carried out at a pH below pH 7, which may include a pH between about pH 5 and about pH 8, or between about pH 5.5 and about pH 7.5, or between about pH 6 and about pH 7, or at about pH 5.5, or at about pH 6.5.

The reducing reaction may be conducted for a time of at least about 5 minutes, about 10 minutes, about 20 minutes, about 30 minutes, about 40 minutes, about 50 minutes, about 60 minutes, about 90 minutes, about 2 hours, about 3 hours, about 4 hours, or about 5 hours. The time of the reducing reaction may be less than about 24 hours, less than about 20 hours, less than about 12 hours, or less than about 6 hours. The reducing reaction may also be conducted for about 1 hour.

The reducing reaction results in the production of a composition that contains a reduced protein having at least one thiol group to which an agent may be linked. Additionally, where trisulfide bonds were present in the isolated protein prior to the reducing step, the resulting composition will also contain reactive sulfide(s).

The reactive sulfide content in the composition produced by the reducing reaction may be decreased by adjusting the pH of the composition to a pH between about 5.0 and about 6.0, or a pH between about 5.2 and about 5.8, or by adjusting the pH of the composition to a pH of about pH 5.5. Conducting the reducing reaction at a weakly acidic pH may reduce the overall efficacy of the reducing reaction, but these weekly acidic reaction conditions also reduce the reactive sulfide content of the composition. Alternatively, the pH of the composition may be adjusted from a neutral pH of about 7.0, to a weekly acidic pH between about 5.0 and about 6.0 after the reducing reaction is complete.

The choice of pH in the reducing reaction will also be influenced by other factors, such as the stability of the isolated protein towards formation of other undesirable derivatives thereof (e.g. dimers or higher oligomers thereof, deamidated forms thereof, sulfoxidated forms thereof, etc.), avoidance of precipitation, and so on, while seeking to minimize the production of reactive sulfide content in the composition.

The reactive sulfide content in the composition produced by the reducing reaction may also be decreased by replacing a certain portion of the liquid in the composition with a fresh or new liquid having substantially reduced or no reactive sulfide content, thereby lowering the reactive sulfide content in the overall composition. This may be accomplished by associating the reduced protein in the composition with the solid support and then washing the reduced proteins with one or more wash steps. The reduced proteins in the composition associated with solid support may be washed with aqueous media that may include one or more of a buffer, a stabilizing agent, pH adjusting agent, a protein denaturing agent, and the like. For example, a PBS wash can be applied after the reduced protein has been associated with a solid support, thereby washing away some or all of the reactive sulfide species present in the composition following the reducing reaction. The wash can also be used, for example, to clear other impurities. A wash with a high salt buffer solution can also be used to promote the clearance of impurities, for example, after the composition comprising the reduced protein is associated with the solid support. It is also possible to use several washes each comprising a different liquid. For example, a high salt wash can be combined with a wash designed to replace the buffer present in the composition or to adjust the pH of the composition prior to the step of conjugating the drug to the reduced protein. Additionally or alternatively, a wash can be applied after the reduced protein has been associated with a solid support to remove the reducing agent from the protein when the reducing reaction is deemed to be complete. Additionally or alternatively, another wash, for example a low salt concentration wash, can be applied to promote efficient disassociation, for example elution, of the reduced protein from the solid support. At least 90% of the composition containing the reduced protein may be replaced with a replacement solution lacking the reactive sulfide.

The solid support may include at least one of a filter membrane, a selectively permeable membrane, and a chromatography resin. Exemplary filtration membranes may include crossflow filtration (also known as tangential flow filtration; TFF) membranes or dead-end filtration membranes. Exemplary selectively permeable membranes may include dialysis, desalting and buffer exchange membranes.

The reactive sulfide content in the composition produced by the reducing reaction is decreased by increasing the mixing rate of the components of the reducing reaction. This increased mixing rate may enable reactive sulfide species to escape the reaction as a gas vented through and open reactor port.

For these reducing reactions, an optimal mixing rate is typically established, wherein a complete or partial reduction of the trisulfide and disulfide bonds present in the isolated protein are economically and efficiently reduced to an average target level of available thiol moieties for subsequent conjugation to drug molecules. The mixing rate may be increased for all or at least a portion of the time of the reducing reaction in order to enhance the elimination of reactive sulfide species from the composition formed during the reducing reaction. For example, the mixing rate may be increased by at least 10%, 20%, 40%, 80%, 100%, 150%, 200%, 250%, 300%, 350%, 400%, 450%, 500%, or 550% above the optimal mixing rate established for the reducing reaction. As another example, the mixing rate may be increased by 2 fold, threefold, 4 fold, or 5 fold above the optimal mixing rate established for the reducing reaction. The mixing rate may also be increased above the optimal mixing rate established for the reducing reaction for less than the full amount of time that the reducing reaction is conducted. The mixing rate may be increased only during the latter portion of the time during which the reducing reaction is conducted. For example, the mixing rate may be increased only during the last half of the time during which the reducing reaction is conducted. Alternatively, mixing rate may be increased only during the last 40%, 30%, 20%, 10%, or 5%, of the time during which the reducing reaction is conducted. In a specific example, the reducing reaction is conducted for 90 minutes and the mixing rate is increased between about 200% and about 500% for the last 5 minutes of the reducing reaction. The mixing rate may also be increased only during the beginning of the time during which the reducing reaction is conducted. For example, the mixing rate may be increased only during the first half of the time during which the reducing reaction is conducted. For example, the mixing rate may be increased only during the first 40%, 30%, 20%, 10%, or 5%, of the time during which the reducing reaction is conducted. In a specific example, the reducing reaction is conducted for 90 minutes and the mixing rate is increased between about 200% and about 500% for the first 5 minutes of the reducing reaction.

The reactive sulfide content in the composition produced by the reducing reaction may be decreased by contacting the composition formed during the reducing reaction with a nitrogen source.

The nitrogen source may include nitrogen gas, as well as air and/or argon gas. The nitrogen source may also include "noble gases" (such as helium (He), neon (Ne), argon (Ar), krypton (Kr) and Xenon (Xe)), notably helium and argon.

The method of contacting the composition formed in the reducing reaction with the nitrogen source may be done, for example, by passing a nitrogen containing gas through the liquid composition (e.g. by sending a stream of gas bubbles into the medium), with or without stirring or other means of mixing, or by other means creating a large liquid phase/gas phase interface at which gas diffusion between phases may occur.

The parameters which may be adjusted in order to reduce the reactive sulfide species in the composition include the duration of contact between the nitrogen containing gas and the liquid composition, the rate of introduction/passage of the nitrogen containing gas into the liquid composition, the mixing rate of the composition with the nitrogen containing gas, the pH of the liquid medium, the temperature of the liquid composition and/or the nitrogen containing gas, the surface area of contact between the gas phase and liquid phase, and the volume of the nitrogen containing gas employed. Additionally, the nitrogen containing gas may be introduced into contact with the liquid composition through a sparge stone, in which case the location and size of the sparge stone are also parameters that may be influential in reducing or eliminating reactive nitrogen species from the composition.

The duration of the contacting between the nitrogen containing gas and the liquid composition, is preferably the time sufficient to reduce or eliminate the presence of reactive sulfide species in the composition. This may be, for example, between about 1 minute and about 240 minutes. The nitrogen containing gas may be brought into contact with the composition of the reducing reaction for the entire duration of the reducing reaction. The nitrogen containing gas may also be brought into contact with the composition of the reducing reaction for only a portion of the time during which the reducing reaction is conducted. The nitrogen containing gas may also be brought into contact with the composition of the reducing reaction after the reducing reaction is considered complete, or stopped by other means, such as buffer exchange to remove the reductant in the composition or by quenching with an agent introduced into the composition to stop the reducing reaction. The nitrogen containing gas may also be brought into contact with the composition of the reducing reaction for only the first portion of the time during which the reducing reaction is conducted. For example, the nitrogen containing gas may also be brought into contact with the composition of the reducing reaction during the first 40%, 30%, 20%, 10%, or 5%, of the time during which the reducing reaction is conducted. The nitrogen containing gas may be contacted with the composition of the reducing reaction for a period of about 30 minutes, about 60 minutes, or about 90 minutes.

The rate of introduction or passage of the nitrogen containing gas into the liquid composition may include a controlled rate of introducing the nitrogen containing gas into the composition of the reducing reaction sufficient to substantially reduce or eliminate the presence of reactive sulfide species in the composition. The nitrogen containing gas may be introduced into the composition at a rate between about 10 cubic centimeters per minute and about 60 cubic centimeters per minute. The nitrogen containing gas may be introduced into the composition at a rate between about 2 liters per hour and about 30 liters per hour, between about 10 l/hr and about 25 l/hr, or between about 15 l/hr and about 20 l/hr. The nitrogen containing gas may be introduced into the composition at a rate between about 0.25 and about 1 (volume of gas/volume of liquid/minute).

The mixing rate of the composition with the nitrogen containing gas, may be a mixing rate sufficient to bring substantially all of the composition of the reducing reaction into contact with the nitrogen containing gas, thereby substantially reducing or eliminating reactive sulfide species present in the composition. The mixing rate of the reducing reaction during the step of contacting the composition with the nitrogen containing gas may be at least 10%, 20%, 30%, 40%, 50%, 100%, 200%, 300%, or 400% greater than the optimal mixing rate for the reducing reaction. The mixing rate of the reducing reaction during the step of contacting the composition with the nitrogen containing gas may be about 200% greater than the optimal mixing rate for the reducing reaction.

The pH of the reducing reaction during the period of time in which the nitrogen containing gas is contacted with the composition may be the optimal pH range for driving the reducing reaction to the desired endpoint of reducing some portion or all of the sulfide bonds present in the isolated protein. This pH range may be adjusted to maintain good yield of the reducing reaction while substantially reducing or eliminating the active self-species present in the composition, in conjunction with contacting of the composition with the nitrogen containing gas. The pH of the reducing reaction may be maintained in a pH range between about pH 4.0 and about pH 9.0 while the nitrogen containing gas is contacted with the composition of the reducing reaction. The pH of the reducing reaction may also be maintained in the pH range between about pH 5.0 and about pH 8.0 while the nitrogen containing gas is contacted with the composition. The pH of the reducing reaction may be maintained in the weekly acidic pH range between about pH 5.0 and about pH 6.0 while the nitrogen containing gas is contacted with the composition.

The temperature of the liquid composition of the reducing reaction and the nitrogen containing gas may be maintained in a temperature range optimal for the reducing reaction. This temperature range may be modified to maintain good yield for the reducing reaction while substantially reducing or eliminating reactive sulfide species in the composition of the reducing reaction, in conjunction with the introduction of the nitrogen containing gas to the composition. The temperature of the liquid composition of the reducing reaction may be maintained at a temperature between about 4° C. and about 40° C. during the time in which the nitrogen containing gas is brought into contact with the composition. The temperature of the liquid composition of the reducing reaction may also be maintained at a temperature between about 15° C. and about 40° C. The temperature of the liquid composition of the reducing reaction may also be maintained at a temperature of about 20° C. or about 30° C.

The reaction conditions of the reducing reaction during the time in which the nitrogen containing gas is contacted with the reaction composition may be adjusted to maintain a surface area of contact between the nitrogen containing gas phase and the liquid reaction phase, in a range that substantially reduces or eliminates reactive sulfide species present in the reaction composition. The ratio of the surface area of the nitrogen containing gas to the volume of the composition is between about 0.1 and about 3. The ratio of the surface area of the nitrogen containing gas to the volume of the composition may be about 2. The volume of the nitrogen containing gas introduced into the liquid composition of the reducing reaction is controlled to maintain the optimal rate and ratio of surface area to volume of liquid reaction components in order to substantially reduce or eliminate reactive sulfide species in the composition of the reducing reaction.

Additionally, the nitrogen containing gas may be controllably introduced into contact with the liquid composition of the reducing reaction through a device that generates gas bubbles of defined size. For example, the nitrogen containing gas may be introduced through an air or "sparge" stone or perforated filter disk. Inert metal sparge stones may be used repeatedly and may be cleaned by acid/base washes and sterilized by autoclaving. The sparge stone may be oriented vertically in the fluid composition of the reducing reaction in such a way that the bubbles formed are allowed to rise directly up into the reaction fluid. The sparge stone may be a stainless steel sparge stone having about 2 micron holes. The sparge stone may have pores that generate air bubbles of <1 mm in diameter at flow rate of up to 5 L/min. The flow rate may be controlled by a mass flow controller placed upstream of the sparge stone.

The introduction of the nitrogen containing gas at certain flowrates and under certain mixing conditions may create a foam in the composition of the reducing reaction, which may reduce the efficiency and/or extent of the reducing reaction. Therefore, when a nitrogen containing gas is introduced into the reducing reaction, the reaction may be conducted in the presence of a tween and/or an antifoaming agent. The reducing reaction may be conducted in the presence of a tween that is at least one of Tween-20 and Tween-80. The reducing reaction may also be conducted in the presence of an antifoaming agent that is at least one of Antifoam-A, Antifoam-C, and poloxamers such as polyethylene oxide.

Conjugation of Reduced Proteins

The therapeutic agent to be conjugated to the protein may be indirectly conjugated with an amino acid side chain of the reduced protein, or an activated amino acid side chain, or a cysteine engineered in the protein, and the like, through a linker. For example, a partially reduced antibody can be conjugated with biotin and an agent can be conjugated with avidin or streptavidin, or vice versa. Biotin binds selectively to streptavidin and thus, the agent can be conjugated with the antibody in this indirect manner.

Drug linker moiety and conjugation methods are disclosed in PCT Publication No. WO 2004/010957, U.S. Pat. Nos. 7,659,241, 7,829,531, and 7,851,437, which are incorporated herein by reference.

Partially reduced antibodies produced by the methods of this invention may also be chemically modified by covalent conjugation to agents that may increase their circulating half-life, including for example, polymers. Exemplary polymers, and methods to attach them to peptides, are illustrated in U.S. Pat. Nos. 4,766,106, 4,179,337, 4,495,285 and 4,609,546, which are incorporated herein by reference. The polymers may include polyoxyethylated polyols and polyethylene glycol (PEG) (e.g., a PEG with a molecular weight of between about 1,000 and about 40,000, such as between about 2,000 and about 20,000).

The agent may be a therapeutic agent selected from a chemotherapeutic agent, a nucleic acid, a cytokine, an immunosuppressant, a radioisotope, an antibiotic, and a therapeutic antibody. The therapeutic agent may be a chemotherapeutic agent. The chemotherapeutic agent may be at least one anti-tubulin agent selected from an auristatin, a vinca alkaloid, a podophyllotoxin, a taxane, a baccatin derivative, a cryptophysin, a maytansinoid, a combretastatin, and a dolastatin. The chemotherapeutic agent may be at least one of an auristatin, a DNA minor groove binding agent, a DNA minor groove alkylating agent, an enediyne, a lexitropsin, a duocarmycin, a taxane, a puromycin, a dolastatin, a maytansinoid, and a vinca alkaloid. The chemotherapeutic agent may be a dolastatin, and particularly an auristatin, and in specific instances, the monomethyl auristatin E (MMAE) or monomethyl auristatin F (MMAF).

The agent conjugated to the at least one thiol group of the reduced protein may form an antibody drug conjugate (ADC), thus comprising both an antibody and a drug, which may be conjugated to each other via a linker.

Suitable linkers for use in the conjugation of drugs to the reduced antibodies in the formation of ADCs according to the methods of this invention include linkers that are cleavable under intracellular conditions, such that the cleavage of the linker releases the drug unit from the antibody in the intracellular environment. Alternatively, the linker may not be cleavable and the drug is, for example, released by antibody degradation. Alternatively, the linker is cleavable by a cleaving agent that is present in the intracellular environment (e.g. within a lysosome or endosome). Thus, the linker can be a peptidyl linker that is cleaved by an intracellular peptidase or protease enzyme, including but not limited to, a lysosomal or endosomal protease. The peptidyl linker may be at least two amino acids long or at least three amino acids long. Cleaving agents can include cathepsins B and D and plasmin, all of which are known to hydrolyze dipeptide drug derivatives resulting in the release of active drug inside the target cells (see e.g. Dubowchik and Walker, 1999, Pharm. Therapeutics 83:67-123). The peptidyl linker cleavable by an intracellular protease may be a Val-Cit (valine-citrulline) linker or a Phe-Lys (phenylalanine-lysine) linker (see e.g. U.S. Pat. No. 6,214,345, which describes the synthesis of doxorubicin with the Val-Cit linker and different examples of Phe-Lys linkers). The linker may be a maleimide functional group that reacts with free thiols to form a covalent bond.

The step of conjugating the agent to the at least one thiol group of the reduced protein may be used to conjugate an anticancer therapeutic agent to an antibody to form at least one of aCD22-val-cit-MMAE, aCD22-val-cit-MMAF, aLy6E-val-cit-MMAE, aLy6E-val-cit-MMAF, aCD79b-val-cit-MMAE, aCD79b-val-cit-MMAF, aNaPi2b-val-cit-MMAE, aNaPi2b-val-cit-MMAF, aMUC16-val-cit-MMAE, a MUC16-val-cit-MMAF, sSTEAP1, and aETBR.

One exemplary embodiment of methods of the invention provides a method for converting trisulfide bonds to disulfide bonds in an isolated antibody by contacting at least one isolated antibody containing at least one trisulfide bond and at least one disulfide bond in a solution with TCEP at a pH between about pH 5.5 and about pH 7.5, and contacting the solution with nitrogen gas, and, conjugating an auristatin, or a derivative thereof, to the reduced antibody to form an antibody-drug conjugate (ADC).

EXAMPLES

The following examples are provided for illustrative purposes only and are not intended to limit the scope of the invention.

Example 1

This example describes the formation of a drug dimer during reduction and conjugation of an antibody (anti-CD79b or anti-CD22) containing varying trisulfide content, to an anti-cancer dolastatin (MMAE) through a Val-Cit (valine-citrulline) linker. These data demonstrate that the drug dimer formation is related to the trisulfide content of the mAb bulk intermediate in this model system.

mAb intermediates (anti-CD79b or anti-CD22) containing different percentages of trisulfide bonds were partially reduced using TCEP and subsequent conjugation reactions were performed with the drug-linker vcMMAE.

Unconjugated mAbs (>5 g/L) were adjusted to a pH between pH 5.5-7.5. Following determination of the protein concentration, the pH-adjusted samples were reduced using a pre-determined TCEP:mAb ratio (from a 10 mM stock solution of TCEP in water) for a target reduction time of 90 minutes at room temperatures. The partially-reduced mAb was immediately conjugated using an excess of the desired maleimide-containing linker-drug. Unreacted linker-drug was quenched with an excess of N-acetyl cysteine (NAC):linker drug ratio (from a 10 mM stock solution of NAC in water) and the pH was adjusted to match the formulation pH conditions. If required, the conjugated sample was buffer exchanged into formulation buffer to remove residual solvents and free drug species that could potentially interfere with subsequent sample analysis. Free drug content in the reduced and conjugated composition was analyzed by RP-HPLC.

Figure 1B:
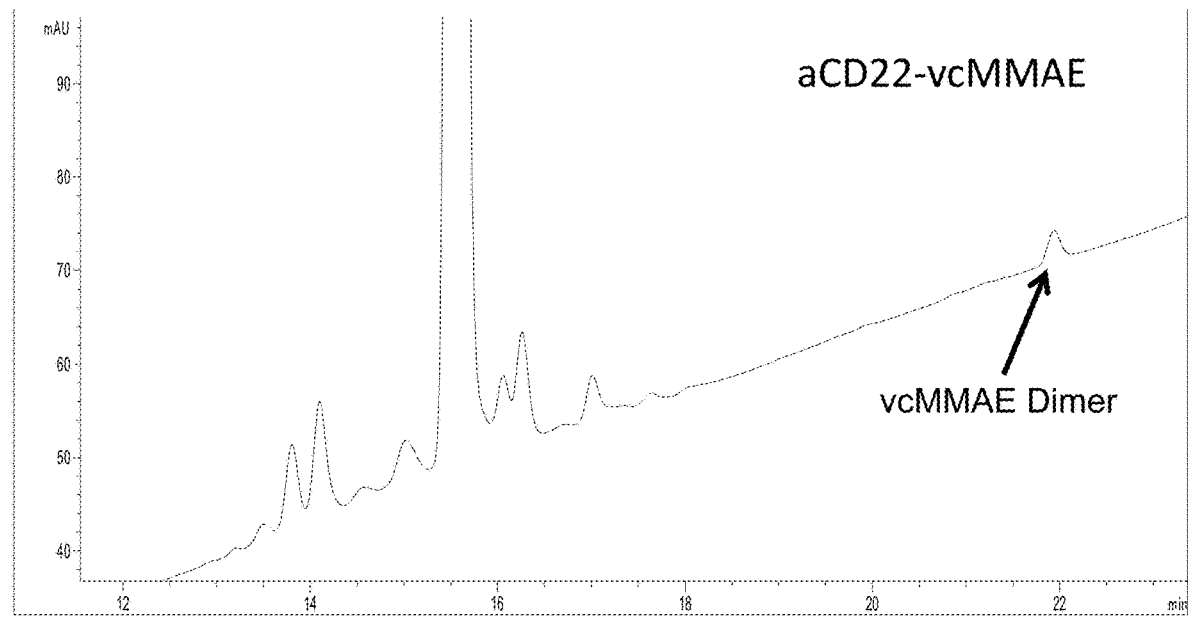

As shown in FIG. 1A, no drug dimer is detected from RP-HPLC analysis of the in-process conjugation pool for aCD79b-vcMMAE conjugate formed from a bulk mAb feedstock containing no trisulfides in the starting mAb. As shown in FIG. 1B, drug dimer (vcMMAE dimer) is detected during analysis of the in-process conjugation pool for aCD22-vcMMAE, containing about 5-6% of measured trisulfides in the starting mAb intermediate.

Example 2

This example describes the analysis of exchanging the buffer following reduction of the partially-reduced protein as a means to reduce or eliminate drug dimer formation in the subsequent conjugation reaction. These data demonstrate that buffer exchange of partially reduced mAb intermediates prior to vcMMAE conjugation reduces drug dimer formation in this model system.

Following partial reduction using TCEP, as described in Example 1, the reduced protein pool was buffer exchanged using centrifugal buffer exchange devices (CENTIRCON™). During buffer exchange using Centricons, both water (buffer) and low molecular-weight solutes are forced through the nominal molecular weight cut-off membrane-filter and collected on the other side (filtrate). The reduced protein remains on the sample side of the membrane (retentate), where it become concentrated to a smaller volume as the water is forced across the membrane to the opposite side. Centricon centrifugal filtration devices with a nominal 10-30 kDa molecular weight cutoff were used per the manufacture instructions. Protein, partially reduced with TCEP (~1-3 mL), as described in Example 1, was added to a single Centricon device and diluted with 10 mM Tris pH 7.5 to a final volume of 10 mL in the device. The Centricon device was centrifuged at 4500 g for 20 minutes. The retentate sample of the Centricon device was further buffer exchanged with 2 additional passes of 10 mL of 10 mM Tris pH 7.5, prior to recovery of the buffer exchanged protein. The buffer-exchanged partially-reduced protein was recovered from the Centricon device and used in subsequent downstream conjugation.

Figure 2A:
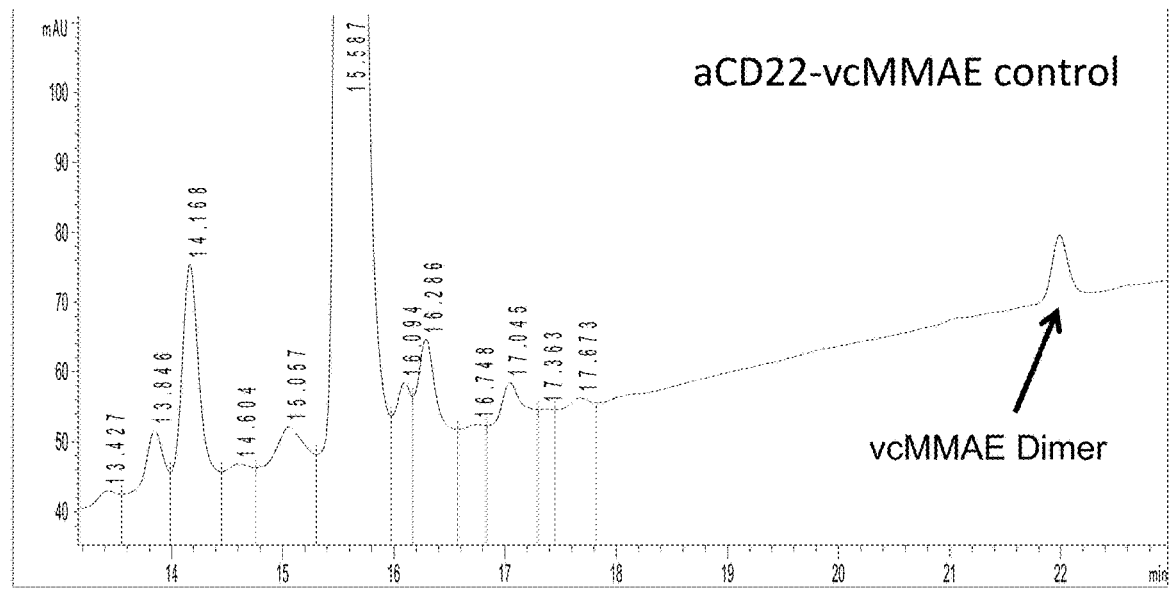
FIGS. 2A and 2B show the measurement of free-drug dimer by RP-HPLC following buffer exchange of partially reduced mAb intermediates containing different percentages of trisulfides, prior to drug conjugation.
Figure 2B:
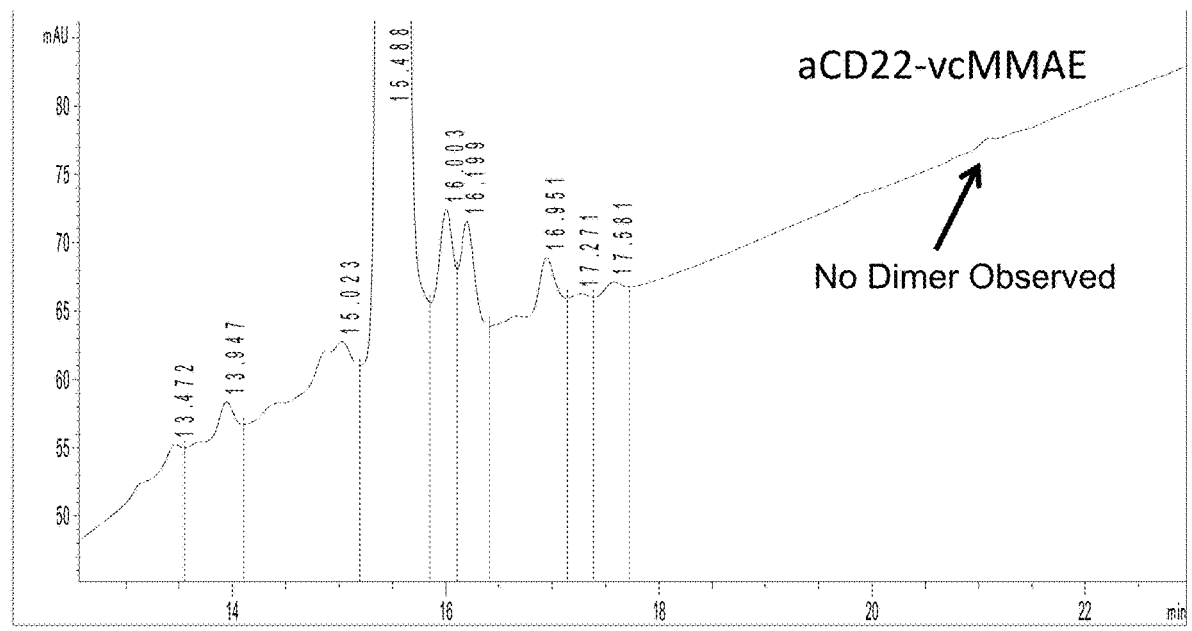
Figure 3:
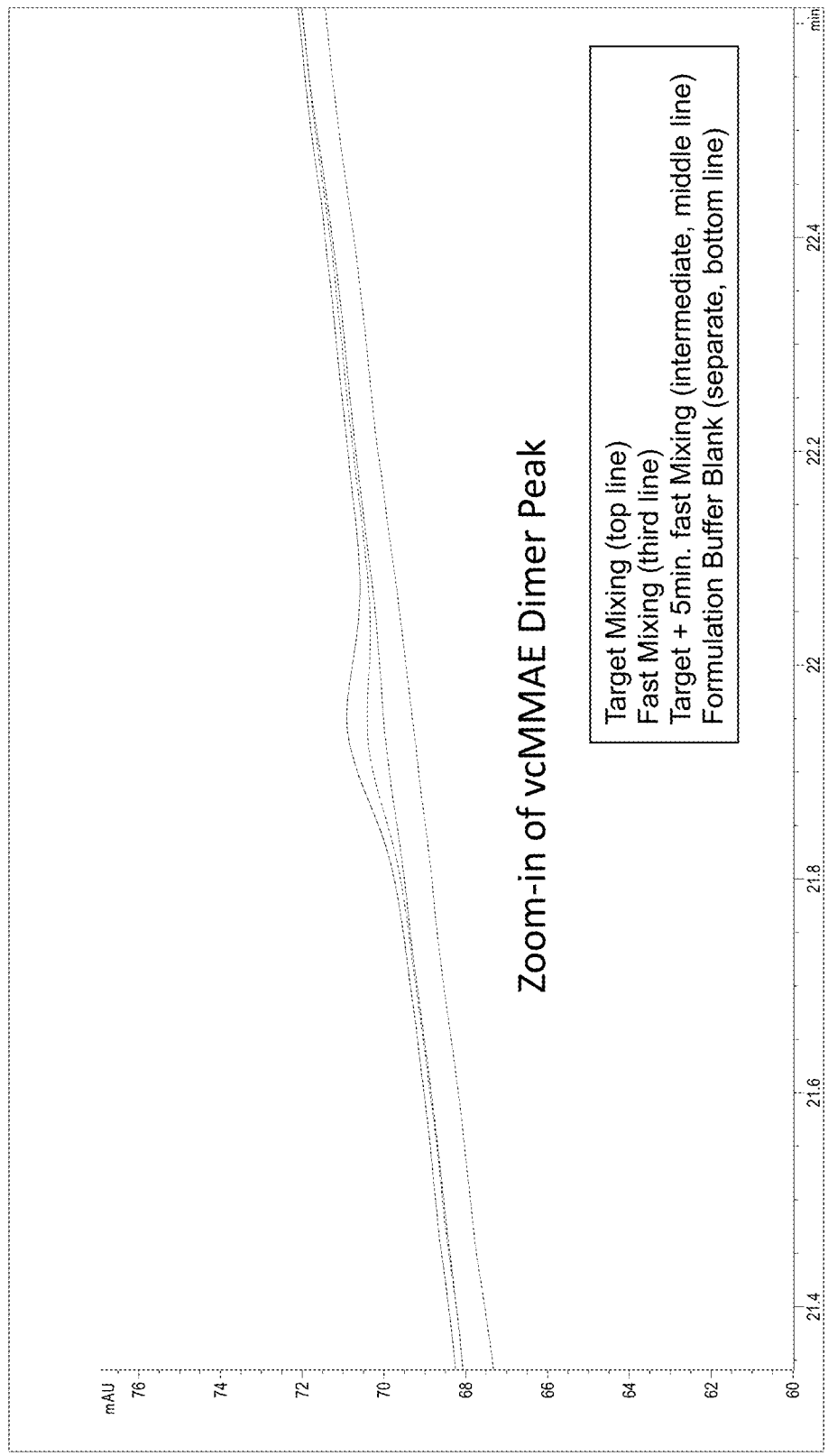
FIG. 3 shows the impact of accelerated mixing during partial reduction of mAb intermediates containing different percentages of trisulfides. Top line shows free drug analysis of the in-process conjugation pool for aMUC16-vcMMAE, using mixing rate of 75 RPM during reduction (target mixing control). Third line shows the same analysis of free-drug dimer when a mixing rate 400 RPM was used throughout the reduction reaction (fast mixing). Intermediate line shows the free drug analysis for a mixing rate protocol that used 75 RPM during 85 minutes of the reduction reaction and a mixing rate of 400 RPM during the last 5 minutes of the reduction reaction (5 min, fast mixing, total reduction time: 90 minutes). Background control is shown in the separate, bottom line, which is the free drug analysis of the Formulation Buffer blank.

Following buffer exchange, the partially-reduced mAb intermediate was conjugated with vcMMAE, and free-drug dimer content was measured by RP-HPLC, as described in Example 1. As shown in FIG. 2A, RP-HPLC analysis of the in-process conjugation pool for aCD79b-vcMMAE antibody-drug conjugate (ADC) results in the formation of free drug dimers (vcMMAE dimer). But, as shown in FIG. 2B, no free drug dimer is detected during RP-HPLC analysis of the in-process conjugation pool for the same aCD22-vcMMAE ADC following buffer exchange of the partially-reduced mAb protein intermediate.

Example 3

This example describes the analysis of increased reaction mixing rate during partial reduction of the protein as a means to reduce or eliminate drug dimer formation in the subsequent conjugation reaction. These data demonstrate that increasing the mixing rate for at least a portion of the time of the reduction reaction of the mAb intermediates, prior to vcMMAE conjugation, can reduce drug dimer formation in this model system.

During partial reduction of the mAb intermediate (anti-MUC16) using TCEP, as described in Example 1, the mixing rate of the overhead stirring apparatus was increased from a target mixing rate, which was previously determined to be optimal for partial reduction of the aMUC16 protein. Mixing rate was controlled by a magnetic stir bar in the 100 mL reactors or by a motor-powered glass agitator in 100 mL EASYMAX™ Reactors. The mixing rate of the magnetic stir bars were dictated by the settings on the magnetic stir plate, with manual adjustments of the rpm to change the mixing rate during reduction. The glass agitators of the EASYMAX were controlled by the instrument software, and the mixing rate was changed manually though the instrument touchpad or through a predetermined setting in the experiment recipe on the accompanying software.

Conjugation reactions proceeded as described in Example 1, using target mixing parameters, and RP-HPLC analysis was conducted as described in Example 1. Referring to FIG.

3, RP-HPLC analysis was conducted on the Formulation Buffer blank as a background control (separate, lower line).

For a mixing rate of 75 RPM throughout the 90 min TCEP reduction reaction (target mixing control), RP-HPLC analysis of the in-process conjugation pool for the aMUC16-vcMMAE shows free drug dimer formation.

For a mixing rate of 400 RPM (fast mixing) throughout the 90 min TCEP reduction reaction, RP-HPLC analysis of the in-process conjugation pool for the aMUC16-vcMMAE shows no free drug dimer is detected.

For a combined mixing rate that included 85 minutes of mixing the TCEP reduction reaction at 75 RPM reduction, followed by increasing the mixing rate to 400 RPM for the last 5 minutes of the reduction reaction (5 min, fast mixing, total reduction time: 90 minutes), RP-HPLC analysis of the in-process conjugation pool for the aMUC16-vcMMAE shows substantial reduction in the formation of free drug dimer.

Example 4

This example describes the analysis of sparging the partial reduction reaction of the protein with nitrogen gas as a means to reduce or eliminate drug dimer formation in the subsequent conjugation reaction. These data demonstrate that sparging the reaction for at least a portion of the time of the reduction reaction of the mAb intermediates, prior to vcMMAE conjugation, can reduce or eliminate drug dimer formation in this model system.

Partial reduction of two model antibodies (anti-CD22 and anti-Ly6E) using TCEP, was conducted as described in Example 1, and further included nitrogen gas bubbled through the reduction pool, just prior to downstream conjugation reactions (using the vcMMAE drug, as described in Example 1). Nitrogen gas was bubbled into the reaction mixture through a polypropylene serological pipette attached to a nitrogen tap via tubing. Prior to sparging the reaction mixture, the flow rate is measured using a gas flow meter. With the flow rate known, the nitrogen gas line is added into the reaction with the lines clamped until the designated start time during reduction. The reaction is sparged until the predetermined end time, the lines are re-clamped, and the pipettes are removed from the reactor. RP-HPLC analysis in the resulting composition of ADC was conducted using RP-HPLC, as described in Example 1.

Figure 4A:
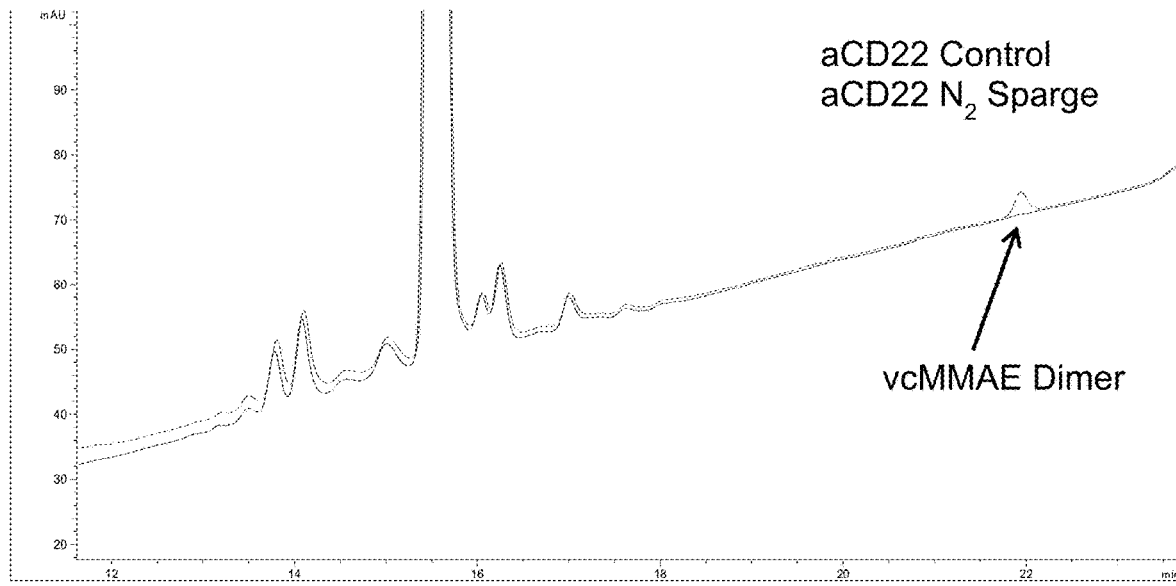
FIGS. 4A and 4B show the impact of N2 gas sparging during partial reduction of mAb intermediates containing different percentages of trisulfides. During the partial reduction reaction, nitrogen gas was bubbled through the reduction pool, just prior to downstream conjugation reactions.
Figure 4B:
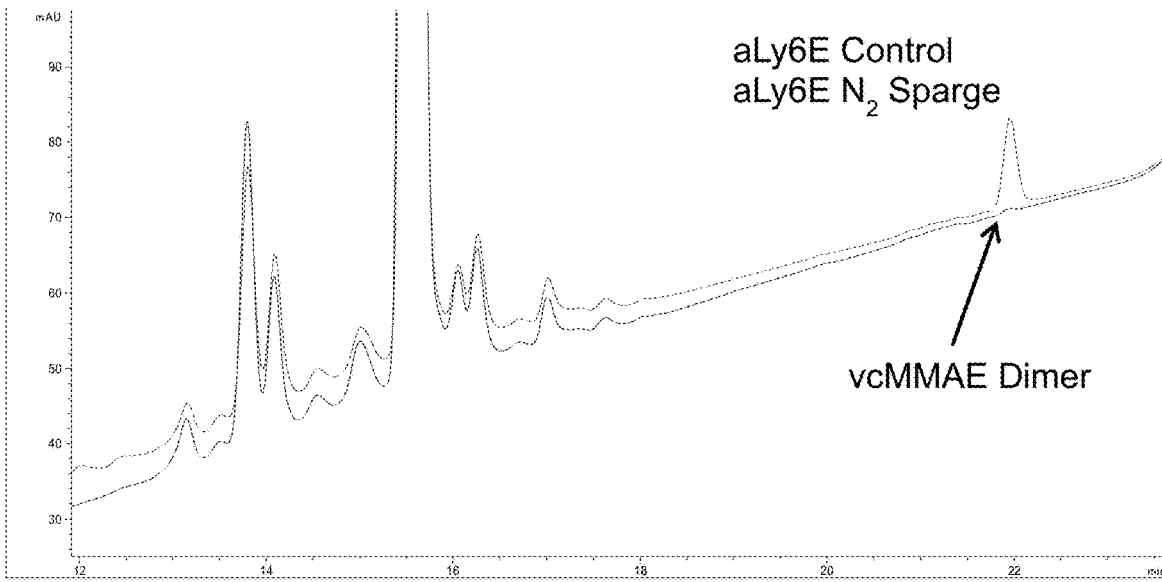

As shown in FIG. 4A, RP-HPLC analysis of the in-process conjugation pool for the aCD22-vcMMAE ADC, with (bottom line) and without (top line) N2 gas sparging during the last 5 minutes of the TCEP partial reduction reaction (total reduction time 90 minutes) demonstrates that nitrogen sparging eliminated free vcMMAE drug dimer formation. Similarly, as shown in FIG. 4B, RP-HPLC analysis of the in-process conjugation pool for the aLy6E-vcMMAE ADC, with (bottom line) and without (top line) N2 gas sparging during the last 5 minutes of the TCEP partial reduction reaction (total reduction time 90 minutes) also demonstrates that nitrogen sparging eliminated free vcMMAE drug dimer formation.

Example 5

This example describes the analysis of sparging a partial reduction reaction of a protein with air as a means to reduce or eliminate drug dimer formation in the subsequent conjugation reaction.

Two 21 mL reduction reductions of a bulk intermediate antibody (anti MUC16) having about 8-12% trisulfides and conjugated with vcMMAE were conducted with reducing agents TCEP or DTT. After reduction each reaction (TCEP and DTT) was split into three pools: 1) a pool that received a 5 min. sparge with nitrogen gas, 2) a pool that received 5 min. sparge with air, and 3) a control reaction that received no sparge of any gas. Specifically, after 85 min. of antibody reduction, the TCEP-reduced and DTT-reduced antibody pools were each split into two 10 mL samples (Samples 1-2) and one 1 mL sample (Sample 3). Sample 1 was sparged with nitrogen for 5 min prior to addition of drug for downstream conjugation. Sample 2 was sparged with air for 5 min prior to addition of drug for downstream conjugation. Sample 3 (control) was not sparged, and held for 5 min prior to addition of drug for downstream conjugation. Following these reduction reactions, the reduced proteins were conjugated with vcMMAE and analyzed for the presence of vcMMAE free drug dimer by RP-HPLC.

Figure 5A:
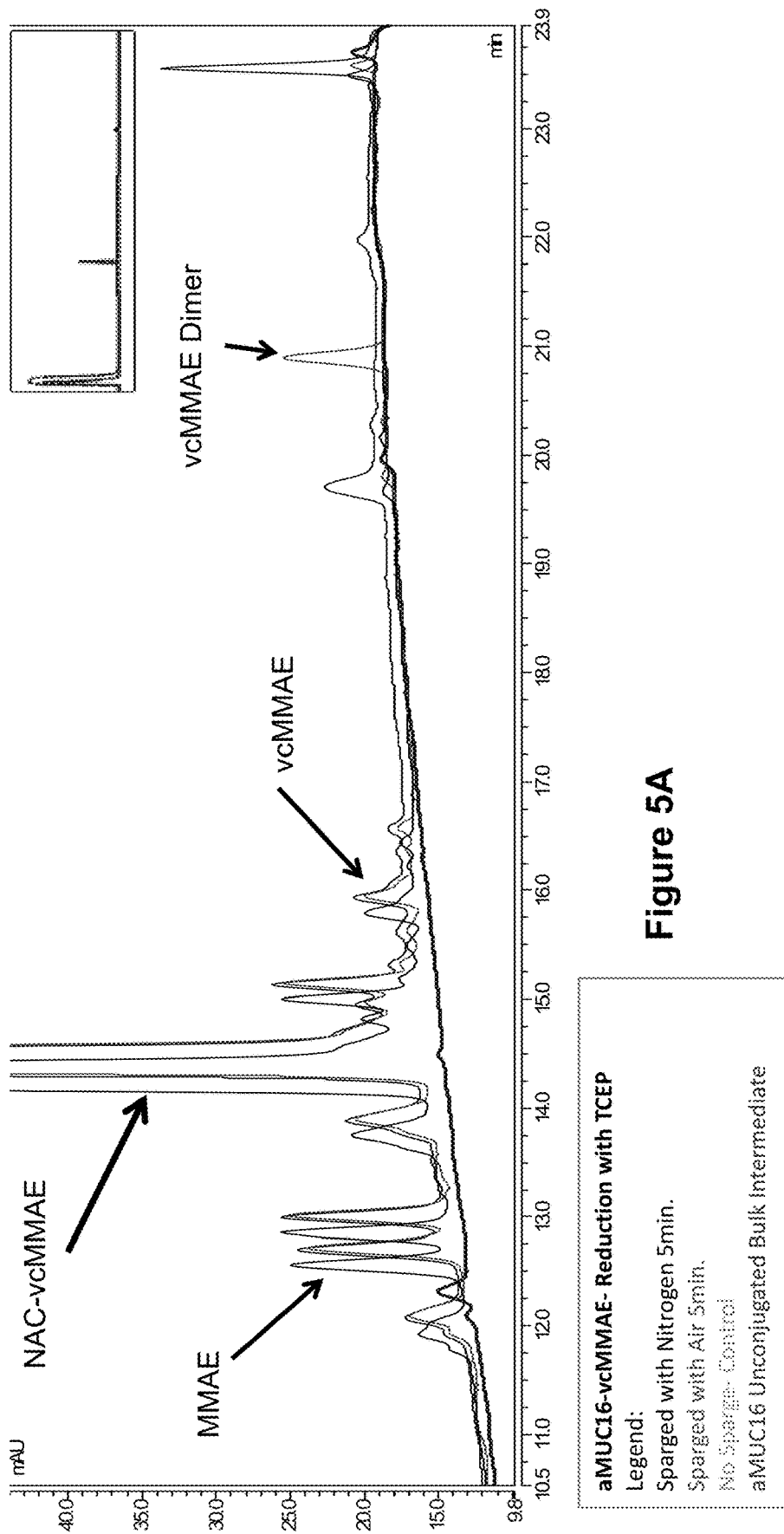
FIGS. 5A and 5B show the results of RP-HPLC assay analysis for the presence, reduction or elimination of free drug dimer.

Each conjugation pool for samples 1-3 were analyzed for the presence, reduction or elimination of free drug dimer using the RP-HPLC assay. As shown in FIG. 5A, for the reactions reduced with TCEP, the vcMMAE free drug dimer impurity is present in the control reaction that received no sparge of any gas and is absent in both the reaction sparged with nitrogen gas and the reaction sparged with air.

Figure 5B:
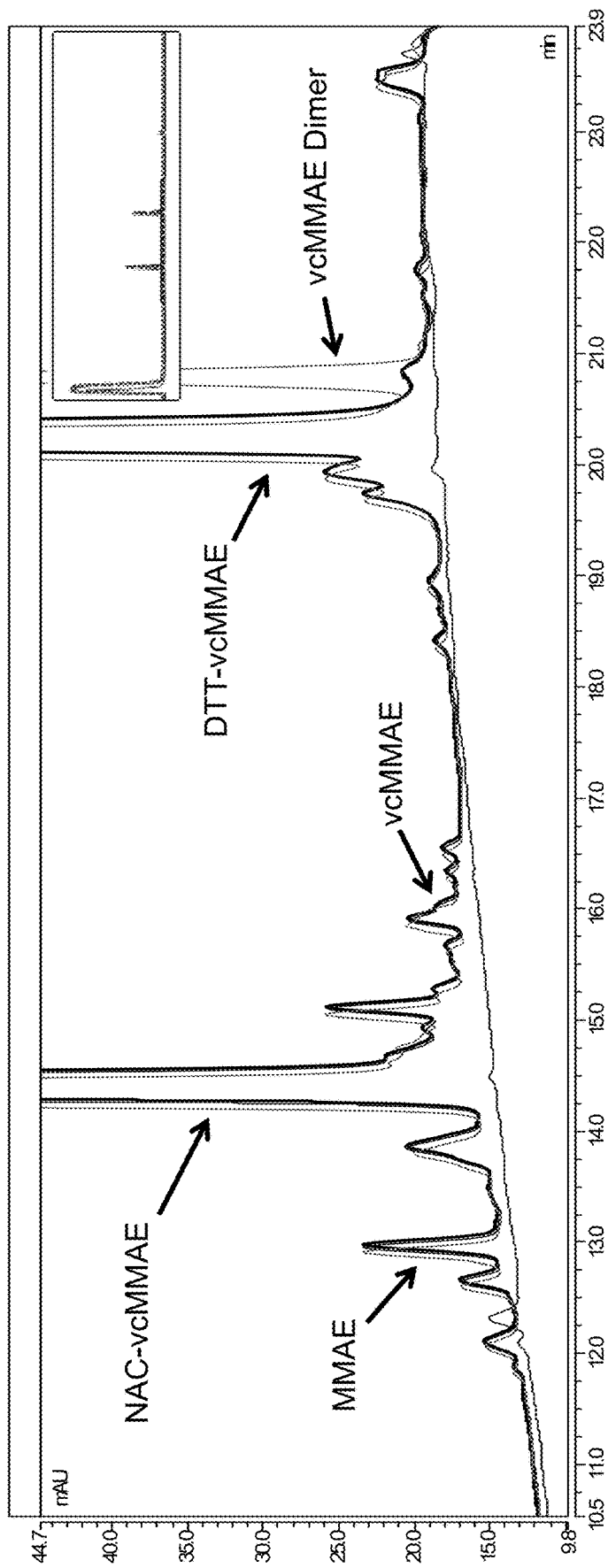

Similarly, for the reactions reduced with DTT, as shown in FIG. 5B, the vcMMAE free drug dimer impurity is present in the control reaction that received no sparge of any gas and is absent in both the reaction sparged with nitrogen gas and the reaction sparged with air. The area under the curve data for these reactions is tabulated in Table 1. Sparging with Nitrogen or Air for 5 min prior to downstream conjugation eliminated formation of free drug dimer species relative to the control no-sparging sample.

TABLE 1

Free drug dimer formation following nitrogen gas or air sparge.

| Sample | | vcMMAE Dimer | |
|---|---|---|---|
| Reductant | Sparge | Ret. Time (min.) | Area (mAU * min.) |
| TCEP | Nitrogen | N/A | 0 |
| | Air | N/A | 0 |
| | Control | 20.893 | 0.8947 |
| DTT | Nitrogen | N/A | 0 |
| | Air | N/A | 0 |
| | Control | 20.788 | 5.5087 |

This data demonstrates the use of thiol reducing agents DTT and TCEP to produce free drug dimer in trisulfide-containing antibodies. Additionally, this data demonstrates that sparging the reduction reaction with air prevents free drug dimer formation during conjugation, similar to result obtained using inert gases such as Nitrogen.

Example 6

This example describes an analysis of the timing of sparging during the reduction reaction of a protein on the reduction or prevention of free drug dimer formation in the subsequent conjugation reaction.

Figure 6:
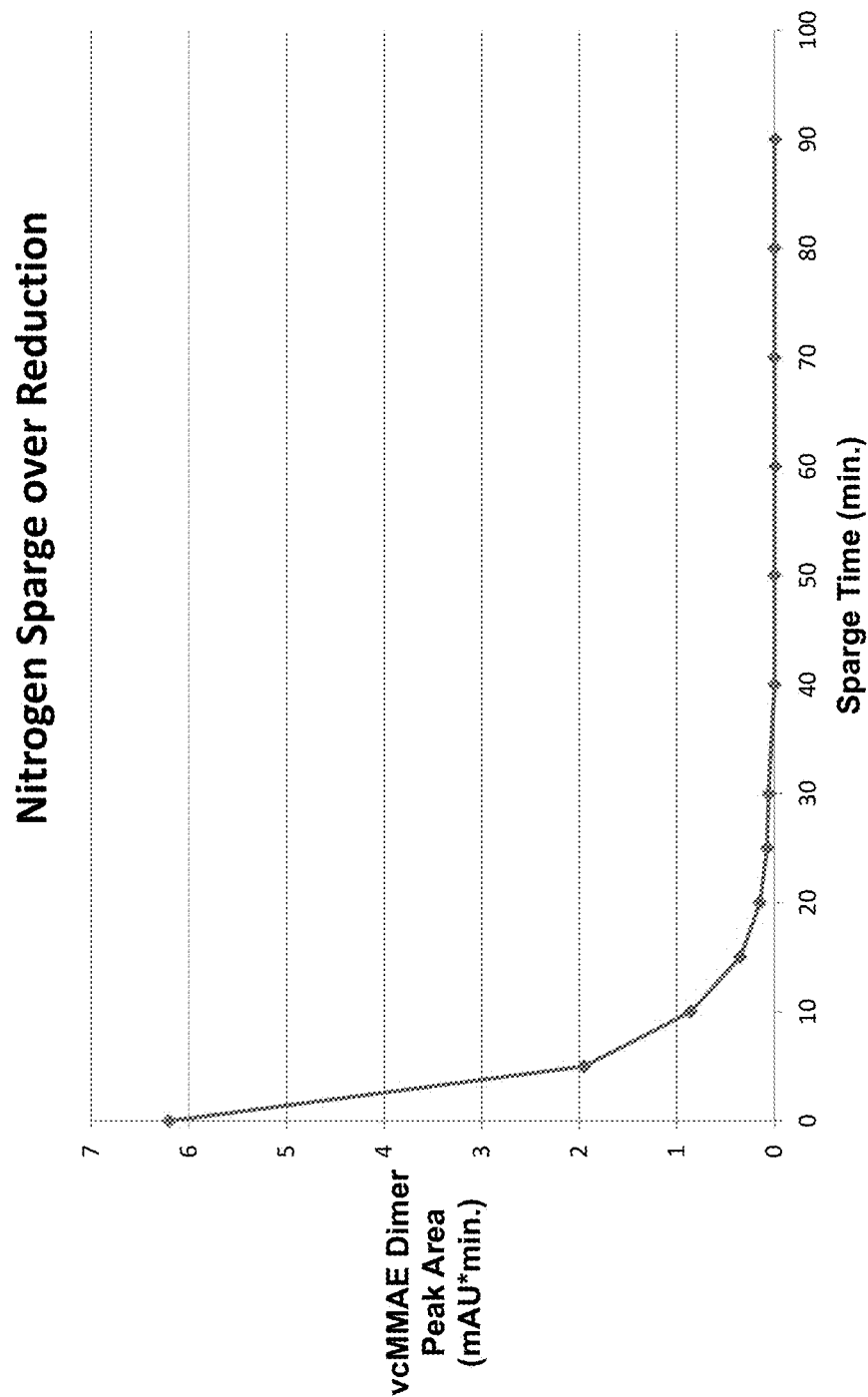
FIG. 6 shows the results of RP-HPLC assay analysis of conjugated samples to monitor the amount of free drug dimer formed, demonstrating that the free drug dimer peak area decreased with increasing sparge time.

To examine the effect of the timing of the Nitrogen gas sparge during the reduction reaction, the sparge time was varied and free and free drug dimer peak area was monitored by RP-HPLC assay. A single 90 mL reduction was performed with a bulk intermediate antibody (anti-Ly6E antibody). Following the addition of TCEP to start reduction reaction, the pool was sparged with nitrogen for the entire 90 min reduction reaction. Samples of the reduction reaction products were taken prior to the start of the sparge as well as during the sparge, and each sample was then conjugated following the sparge. Each conjugated sample was analyzed by the RP-HPLC assay to monitor the amount of free drug (vcMMAE) dimer formed. As shown in FIG. 6, and tabulated in Table 2, the free drug dimer peak area decreases with increasing sparge time.

TABLE 2

Free drug dimer formation following variable sparge time.

| Sparge Time (min.) | vcMMAE Dimer Peak Area (mAU * min) |
| --- | --- |
| 0 | 6.2005 |
| 5 | 1.9524 |
| 10 | 0.8626 |
| 15 | 0.3504 |
| 20 | 0.1493 |
| 25 | 0.0769 |
| 30 | 0.0621 |
| 40 | 0 |
| 50 | 0 |
| 60 | 0 |
| 70 | 0 |
| 80 | 0 |
| 90 | 0 |

These data demonstrate that the free drug dimer is eliminated after 30 minutes of sparge. The data also demonstrate that sparge at the start of reduction effectively reduces free drug dimer formation, and therefore the sparge may occur at the beginning or towards the end of the reduction reaction with similar results.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A method of conjugating a therapeutic agent to a thiol moiety in an isolated protein that contains at least one disulfide bond and at least one trisulfide bond, comprising the steps of:
    (a) reducing at least one sulfide bond in the isolated protein in a reaction composition comprising 0.1 mM to 8 mM tris(2-carboxyethyl)phosphine (TCEP) and weakly acidic pH between pH 5.0 and 6.0, to form a composition comprising a reactive sulfide and a reduced protein comprising at least one thiol group;
    (b) decreasing the reactive sulfide content of the composition by contacting the composition with a nitrogen source; and
    (c) conjugating the therapeutic agent to the at least one thiol group of the reduced protein to form a protein-agent conjugate.

2. The method of claim 1, wherein the reducing step comprises at least partial reduction of the at least one sulfide bond by contacting the isolated protein with a reducing agent.

3. The method of claim 1, wherein the isolated protein comprises at least 4 disulfide bonds.

4. The method of claim 1, wherein the isolated protein comprises at least 2 trisulfide bonds.

5. The method of claim 1, wherein, prior to the reducing step, between about 1% and about 20% of the sulfide bonds in the isolated protein are trisulfide bonds.

6. The method of claim 1, wherein the reducing step is conducted under non-denaturing conditions.

7. The method of claim 1, wherein the nitrogen source comprises nitrogen gas.

8. The method of claim 7, wherein the contacting comprises bubbling the nitrogen gas through the composition.

9. The method of claim 1, wherein the contacting comprises sparging the composition with at least one of nitrogen gas, and air.

10. The method of claim 1, wherein the contacting comprises sparging the composition with nitrogen gas at a rate between about 10 cubic centimeters per minute and about 60 cubic centimeters per minute.

11. The method of claim 1, wherein the contacting comprises mixing the composition in the presence of nitrogen gas at a rate that is at least 200% greater than the optimal mixing rate for the reducing step.

12. The method of claim 1, wherein the contacting is conducted at a pH between about 5.0 and about 8.0.

13. The method of claim 1, wherein the contacting is conducted at a temperature between about 4° C. and about 40° C.

14. The method of claim 1, wherein a ratio of the surface area to the volume of the composition is about 2.

15. The method of claim 1, wherein the contacting comprises introducing a nitrogen gas into the composition during the reducing step for a time that is less than a time for conducting the reducing step.

16. The method of claim 1, wherein the contacting is conducted in an open reaction vessel, wherein reactive sulfide is vented from the composition.

17. The method of claim 1, wherein the contacting comprises sparging a vessel containing the composition with at least one of nitrogen gas, and air.

18. The method of claim 1, wherein the contacting is conducted in the presence of at least one of a tween and an antifoaming agent.

19. The method of claim 1, wherein the isolated protein is an antibody or antibody fragment.

* * * * *